United States Patent [19]

Baker et al.

[11] 4,312,593
[45] Jan. 26, 1982

[54] DIRECT READOUT APPARATUS FOR MEASURING LIGHT TRANSMITTED THROUGH LIQUIDS

[75] Inventors: William B. Baker, Newark, Del.; Joe T. May, Fairfax, Va.

[73] Assignee: E. I. Du Pont de Nemours and Company, Wilmington, Del.

[21] Appl. No.: 106,252

[22] Filed: Dec. 21, 1979

[51] Int. Cl.³ .............................................. G01J 3/50
[52] U.S. Cl. ................................... 356/414; 356/418; 356/243; 356/246
[58] Field of Search ............... 356/414, 416, 418, 432, 356/436, 437, 440, 443, 243, 246

[56] References Cited

U.S. PATENT DOCUMENTS

| | | | |
|---|---|---|---|
| 3,580,683 | 5/1971 | Schulkind | 356/414 |
| 3,840,305 | 10/1974 | Sacarisen | 356/432 |
| 3,942,898 | 3/1976 | Anderson | 356/443 |
| 4,053,235 | 10/1977 | Hampton et al. | 356/418 |
| 4,066,362 | 1/1978 | Carter | 356/246 X |
| 4,066,412 | 1/1978 | Johnson et al. | |

OTHER PUBLICATIONS

*Encyclopedia of Chemical Technology*, Kirk–Othmer, 7th Edition, vol. 5, pp. 794–800.
Witherell et al., *Applied Optics*, Jan. 1970, vol. 9, pp. 73–78.
"Methods Based on Absorption of Radiation," Chapter 28.
"Determination of Trace Elements by Absorption Spectrophotometry, General Concepts," Chapter VI.
P. H. Wendland, "Silicon Photodiodes Come Into Their Own," Reprint from *Optical Spectra*, Oct. 1, 1973.
"Concentration Colorimeter," Model 53A Bulletin No. CC-3, Jun. 1975 by Glenco Scientific, Inc.
Model 440 Absorbance Detector by Waters Associates, Inc. Bulletin, Mar. 1975.
Model 151 and 152 Block Diagram Altex/Beckman Instruments.
Partial Schematic Diagrams Figs. 3 and 4 from Pye Unicam Spectrophotometric L. C. Detector Circuit.

*Primary Examiner*—F. L. Evans
*Attorney, Agent, or Firm*—Hilmar L. Fricke

[57] ABSTRACT

An apparatus that measures light transmitted through a fluid sample and provides a direct readout of such a measurement by electronically converting light transmitted to an electrical signal that is displayed on a readout device; the apparatus contains a power source, a light source, a photodetector, a sample holder for samples that forms a cell; the improvements used in the apparatus are as follows:

(a) a color interference filter positioned between the sample and the photodetector which filters out unwanted bands of color,
(b) a converter which electronically converts a current signal from the photodetector to a voltage signal,
(c) a logarithmic response circuit that changes the voltage signal to a logarithmic signal proportional to the logarithm of the voltage signal; and
(d) a digital voltmeter that converts the logarithm signal to a signal that is displayed on a readout device.

4 Claims, 4 Drawing Figures

DIRECT READOUT APPARATUS FOR MEASURING LIGHT TRANSMITTED THROUGH LIQUIDS

BACKGROUND OF THE INVENTION

This invention relates to an apparatus that measures light transmitted through a fluid sample and in particular to an apparatus that provides a direct readout of transmitted light.

For monitoring air which workers are exposed to during a work period, workers wear chemical badges that are pouches filled with a chemical solution which will absorb certain gases such as sulfur dioxide or nitrogen dioxide. At the end of the work period, the badges are turned in for analysis. To analyze the badges, sealed packets of reagents contained in the pouches are broken and mixed with the chemical solution. If a gas has been absorbed in the chemical solution, the solution changes color. A photometric analysis of the solution is then done and the results recorded. If a worker has received an excessive dosage of a certain gas or the accumulative dosage exceeds a given safe level, the worker is not allowed to work in an area that contains the gas for a prescribed time.

A photometric analysis apparatus has been used to measure light transmission through fluid samples as shown in Carter U.S. Pat. No. 4,066,362 issued Jan. 3, 1978. While this is an excellent apparatus, it does not readily lend itself to an average plant operation since care must be taken to avoid leakage of outside light in the area in which the sample is positioned and no provisions are made to readout data directly in units established by industrial and government agencies. The apparatus of this invention avoids the aforementioned problem and reads out photometric analysis data directly over a wide range in established units.

SUMMARY OF THE INVENTION

An apparatus that measures light transmitted through a fluid sample by a photodetector and converts a signal from the photodetector to a signal that is displayed on a direct readout device; the apparatus contains a power source, a light source electrically connected to the power source, a photodetector, a sample holder for samples that forms a cell of constant thickness through which light from the light source passes and is measured by the photodetector and a readout device; the improvement used in the apparatus in the absence of a reference lightbeam is as follows:

(a) a color interference filter that is positioned between the sample holder and the photodetector that filters all colors from the light transmitted through the sample except a band of colored light that is to be measured;

(b) a converter electrically connected to the photodetector that converts a current signal from the photodetector to a voltage signal;

(c) a logarithmic response circuit electrically connected to the converter that changes the voltage signal from the converter into a logarithm signal proportional to the logarithm of the voltage signal; and (d) a digital voltmeter electrically connected to the logarithmic response circuit that converts the signal from the logarithmic response circuit to a signal displayed on the readout device.

DETAILED DESCRIPTION OF THE INVENTION

Figure 1:
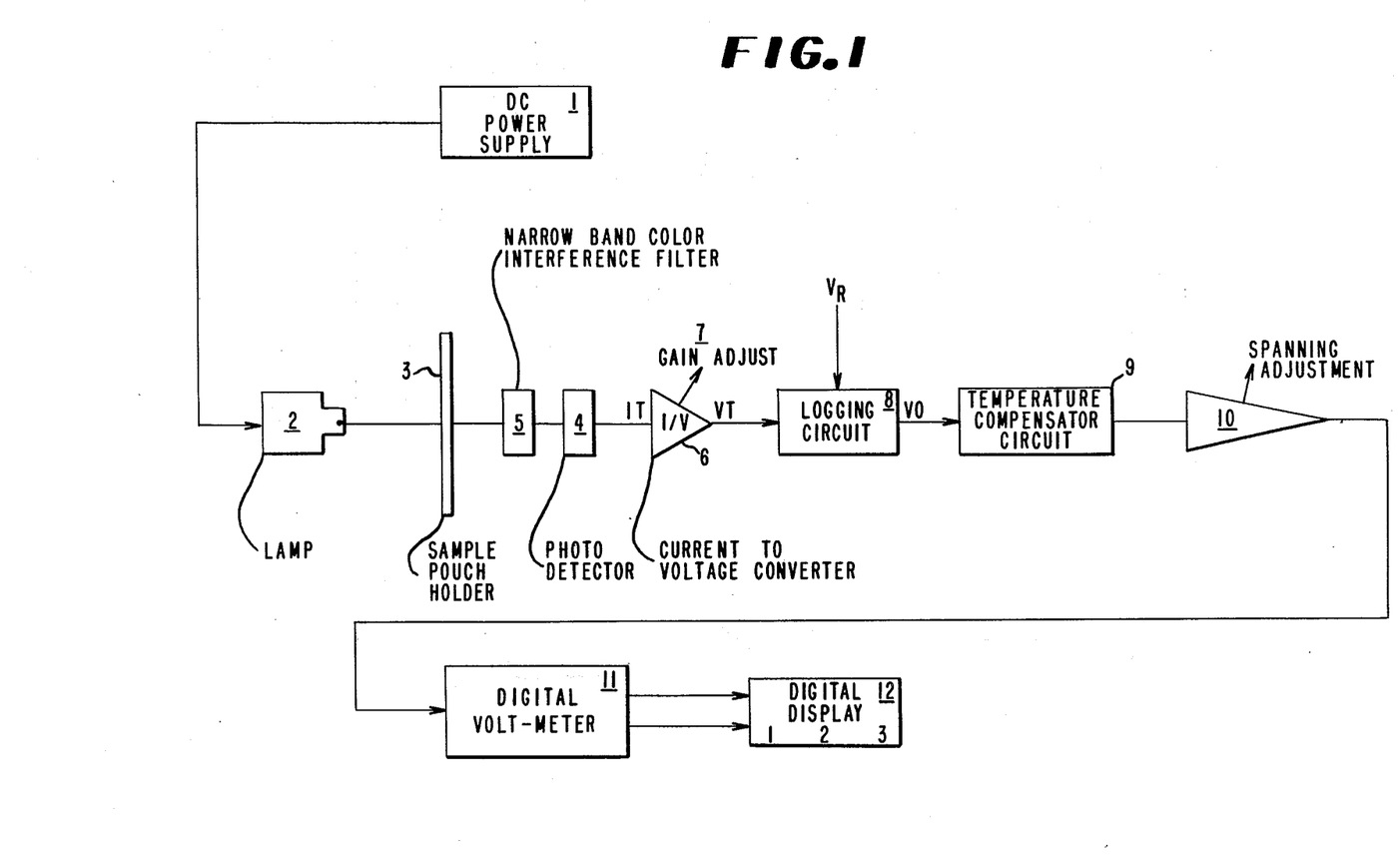
FIG. 1 is a simplified block diagram of the apparatus.

FIG. 1 illustrates a simplified block diagram of the apparatus of this invention. The components illustrated in the block diagram are positioned in a metal housing with an opening for a sample pouch holder that contains a sample pouch. A direct digital readout display, an on-off power switch, a gain dial, a spanning adjustment dial and a selector switch also are provided. A DC power supply 1 that provides 7–12 volts direct current is electrically connected to a lamp 2, typically a tungsten halogen lamp. The DC power supply is a rectifier that converts 115 volt AC current to DC current. A sample pouch in a sampler pouch holder 3 is positioned between the lamp 2 and the photodetector 4. A narrow band color interference filter 5 which typically passes only a narrow band of light of $\pm 15$ nm (nanometers or meters $\times 10^{-9}$) wavelength is positioned between the sample pouch and holder 3 and the photodetector 4.

Light from the lamp passes through the sample pouch in the holder and the interference filter which passes only a narrow band of light through to the photodetector. The light causes an electric current to be generated by the photodetector 4 which is fed into a current to voltage converter (I/V) 6 which has a gain adjust 7. This gain adjust serves as a zeroing control. The signal from the current to voltage converter 6 is fed into a logging circuit 8. In the logging circuit or logarithmic response circuit, the electrical signal is converted to a logarithmic signal. This signal is then fed into a temperature compensator circuit 9 which eliminates any variations in the signal caused by temperature changes. The signal is then fed into a spanning adjustment 10 that is an amplifier with variable gain which converts the output signals from the temperature compensator to a signal that is fed into a digital voltmeter 11. The digital voltmeter provides a signal that is fed to a digital display 12 which can be read directly by an operator.

Figure 2:
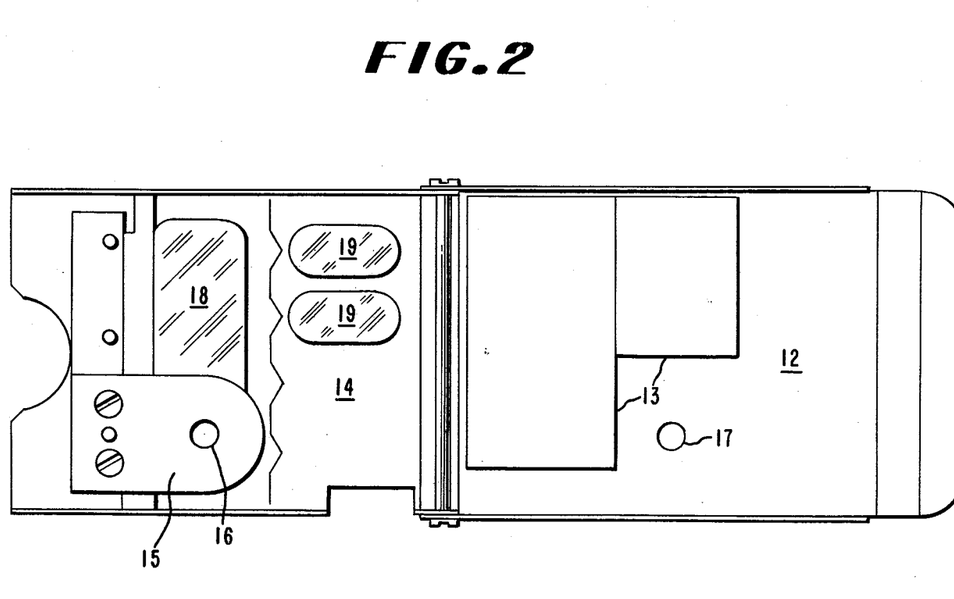
FIG. 2 illustrates a sample pouch and holder.

FIG. 2 illustrates the sample pouch holder. The case 12 of the sample pouch holder can be of metal or a durable plastic. The case has a hinge in the center and folds together. The pressure pads 13 force liquid in the sample pouch 14 into a space under the path length stop 15 which forms a cell of constant thickness through which a light beam is passed from the lamp described in FIG. 1. It is important that a cell is formed of constant thickness to provide accurate readings by the apparatus. The light beam passed through openings 16 and 17 when the sample pouch holder is closed. An opening not shown in the figure is directly opposite opening 16. These openings are covered with a plastic material, preferably a polyethylene terephthalate film to prevent expansion of the pouch into the opening. The sample pouch 14 made of a plastic material contains a section 18 containing liquid which absorbs particular gases to which a worker is exposed. Before placing the sample pouch into the sample holder, a temporary seal on two pouches 19 containing reagents are broken and the reagents are forced into section 18 of the pouch and thoroughly mixed. Sample pouches can contain multiple reagent pouches. The reagent reacts with the liquid which has absorbed gases and a color change occurs and the apparatus measures the intensity of the color of the liquid in the sample pouch. The sample pouch may contain gels, solids or even gases which change color and are not limited to liquids.

The following provides the theory and overall description of the operation of the apparatus.

As mentioned above, the apparatus accurately measures through a color change the amount of a certain gas which has been absorbed by a sample pouch. Beer-Lambert's Law, set forth in mathematical equation (1), is the basis for the operation of the apparatus.

$$c = k \log (\lambda T/\lambda I) \qquad (1)$$

where:
- $c$ = molecular concentration of chemical being sought, PPM/VOL (parts per million/volume)
- $k$ = constant of proportionality, (PPM/VOL)
- $\lambda_T$ = light transmitted by sample in (watts/CM$^2$)
- $\lambda_I$ = light incident on sample in (watts/CM$^2$)

Referring to FIG. 1, the lamp 2 impinges light on the sample pouch 3. The impinged light is $\lambda_I$. The liquid in the pouch absorbs certain colors of light. The color of the light absorbed is dependent on the type of chemical absorbed by the pouch while the depth (amount) of absorption is a function of the amount of chemical absorbed.

The light transmitted by the pouch ($\lambda_T$) is passed through a narrow band color interference filter 5. The filter passes a narrow portion of the light spectrum while blocking all others. The type filter is chosen based on the chemical desired to be detected. The filter is placed before the photodetector to reduce the effect of stray light which may enter around the sample holder and obviates the need for light tight housing and sample holder.

A wide range photodetector converts $\lambda_T$ signal to a current, $I_T$, proportional to $\lambda T$. $I_T$ is passed into an operational amplifier connected as a variable gain current-to-voltage converter 6. Here $I_T$ is converted to a voltage $V_T$ which is directly proportional to $\lambda_T$.

The value of $V_T$ can typically vary over 6 to 7 orders of magnitude, for example, from about 3 volts down to $10^{-6}$ volts. The following techniques are used to reduce this range of variation since this range of variation would place extreme requirements on the electronics of subsequent signal processing stages:

1. The amount of $\lambda_T$ decreases about two orders of magnitude between 700 nm and 350 nm due to reduction in output of the lamp at shorter wavelengths. To compensate for this reduction, the voltage applied to the lamp is increased from 7 V at 700 nm to 12 V at 350 nm which increases $\lambda_I$. The voltage increases light output by a factor of about 10. Also, a filter can be used that increases the band of light passed through from ±10 nm at 700 nm to ±30 nm at 350 nm. This increases the amount of available light by a factor of three between 700 nm and 350 nm.

2. A converter amplifier can be connected to provide a variable gain range of 160 to 1. By proper gain choice, the output of the current to voltage (I/V) converter can be adjusted to 3 V at maximum $\lambda_T$ and since the range of light values for a given pouch is only 100 to 1, the corresponding voltages at the output of the current to voltage converter (I/V) converter is only 3 V to 30 MV. The performance requirement on the I/V converter is relatively modest and a less expensive amplifier can be used.

The output of the I/V converter is connected directly to a logging circuit 8. Its transfer function is as given in equation (2).

$$V_o = k/\log (V_T/V_R) \qquad (2)$$

where:
- $V_o$ = output of logging circuit, volts
- $k$ = constant of proportionality, −3 MV/db
- $V_T$ = output of I/V converter proportional to $\lambda_T$, volts
- $V_R$ = reference voltage against which all output voltages from the I/V converter are compared, volts (this level corresponds to $\lambda_I$)

The function of the logging circuit is to implement the $$\left( \log \frac{\lambda_T}{\lambda_I} \right)$$

portion of the Beer-Lambert Law. The output of the circuit has a negative temperature coefficient and a small scale factor. The temperature coefficient is corrected using a temperature compensator circuit following the logging circuit and the scale factor is increased by a factor of 36 to provide a stronger signal.

The output signal of the temperature compensator drives a variable gain amplifier (spanning adjustment 10) whose gain can be varied over a 800:1 range and its function is to convert the signal directly into engineering units. The signal from the spanning adjustment is fed to the digital voltmeter 11 which converts the signal to a signal which is fed to a digital display which can be readout directly by an operator.

A conventional technique which could be used to bring the apparatus to a zero reading provides for using the signal level from the I/V converter and adjusting $V_R$ into the logging circuit to obtain a zero at the output of the logging circuit. Zero occurs when $V_R$ = output of I/V converter because log 1 = 0. This approach involves a very wide range of signal levels from microvolts to volts but does not work very well since the logging circuit in incapable of accurate operation over such a wide range.

The following technique is used to obtain a zero reading in the apparatus. The reference $V_R$ is fixed at approximately 3 V and the gain of the I/V converter is varied to obtain an output level equal to $V_R$ which gives a zero reading. Zeroing by varying gain allows the circuit to operate at high levels, thus decreasing electrical noise effects, and also makes the logging circuit operate over only two orders of magnitude instead of 4 or 5.

The photodetector operating range is adjusted by varying the lamp voltage and bandwidth of the filters. This reduces the range over which the photodetector must operate by about 2½ orders of magnitude and the speifications for the photodetector can be reduced which in turn reduces the cost of the apparatus.

Figure 3:
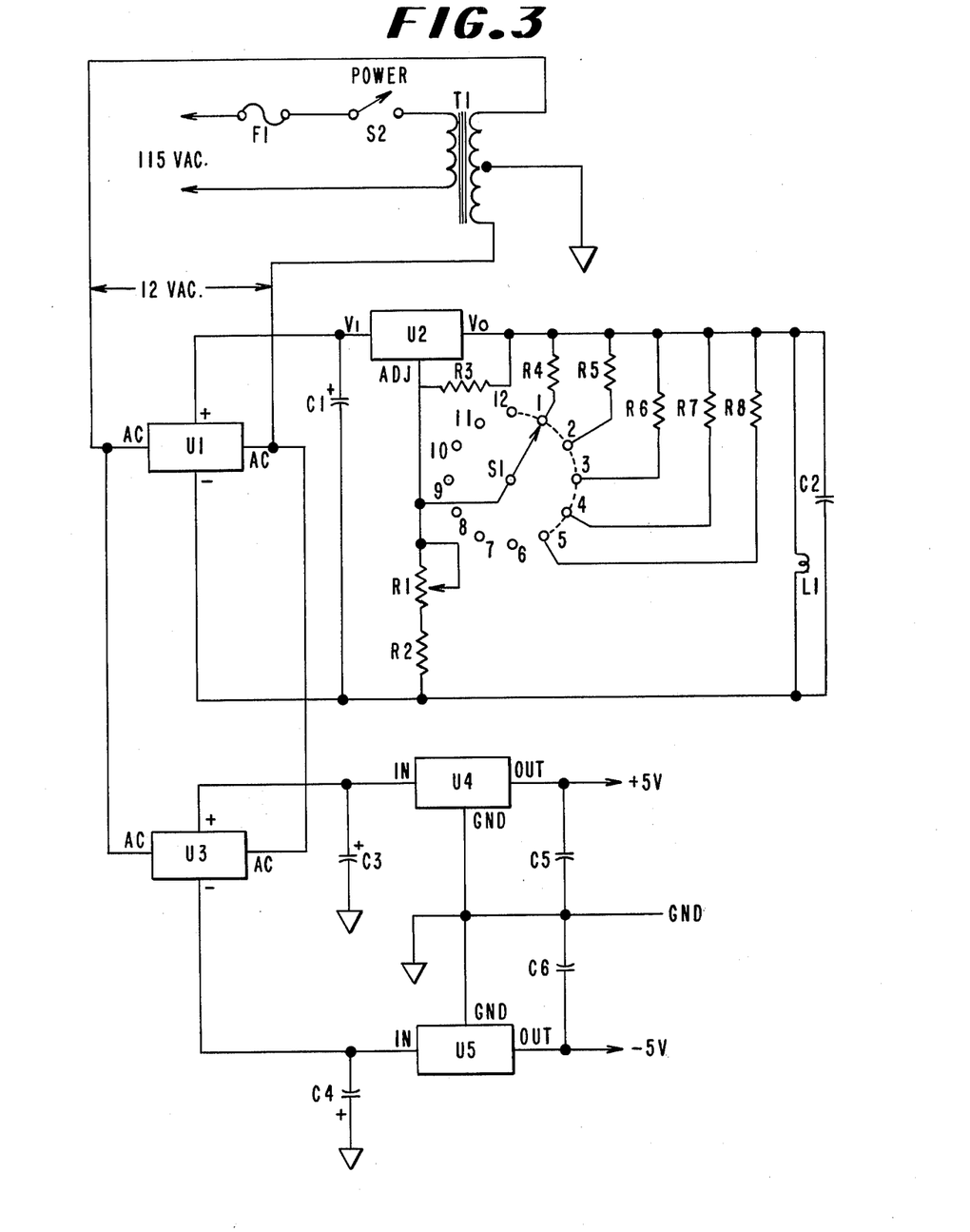
FIGS. 3 and 4 are schematic circuit diagrams for the apparatus.

FIG. 3 is a schematic circuit diagram of the power supply of the apparatus. One hundred fifteen volt AC (115 VAC) power is brought into the apparatus and applied to the primary of transformer, T1 (typically an EWC model DPC-12-2000), through a On/Off switch, S2, and fuse, F1. T1's secondary windings produce 12 VAC across full wave bridge rectifier U1 (typically an Motorola MDA-100). U1 converts the 12 VAC to full wave rectified DC voltage which is stored and filtered in capacitor C1 [typically 2×2200 uf (microfarad)]. The capacitor charges to a peak value of approximately 18 volts. This filtered voltage ($V_f$) is applied to a variable voltage regulator, U2 (typically a National Semiconductor LM 350). The regulator, U2, produces a controlled output voltage ($V_o$) whose value is determined by equation (3):

$$V_o = 1.25 \left[ 1 + \frac{R1 + R2}{Ry} \right] \quad (3)$$

For various positions of switch S1, different values of resistor, RY, are connected between the output terminal of $U_2$ ($V_o$) and its adjustment terminal (ADJ). When the switch is in position 1, RY is represented by the parallel combination of resistor $R_3$ (typically 523 ohms) connected between terminal $V_o$ and ADJ and resistor $R_4$ (typically 619 ohms) connected between switch terminal and $V_o$. In position 2, RY is represented by the parallel combination of $R_3$ and $R_5$ (typically 698 ohms) connected from terminal 2 and $V_o$. In position 3, RY is represented by the parallel combination of $R_3$ and $R_6$ (typically 909 ohms) connected from terminal 3 to $V_o$. In position 4, RY is represented by the parallel combination of $R_3$ and $R_7$ (typically 1.62 K ohms) connected from terminal 4 to $V_o$. In position 5, RY is represented by the parallel combination of $R_3$ and $R_8$ (typically 3.01 K ohms) connected from terminal 5 to $V_o$. In position 6 through 12, no further resistors are connected to these terminals. Therefore, RY is equal to $R_3$. The various values of resistors change the apparent value of RY in the equation and thus use various output voltages for various switch positions. The values vary from 12 volts in position 1 to approximately 7 volts in position 12.

The output voltage ($V_o$) of the regulator, U2, is connected across the lamp, L1 (typically a G.E. No. 789) and hence, its brightness changes with the changing switch positions. The switch also chooses the various color interference filters. Capacitor C2 (typically a 10 uf, 15 Volt) connected across lamp L1, ensures electrical stability of the regulator.

The AC voltage from the secondary of transformer T1 is also connected across a full wave bridge rectifier, U3 (typically a Motorola MDA-100). U3 provides full wave rectified voltage at its "+" and "−" terminals. The "+" terminal of U3 is connected to the +side of capacitor C3 (typically 1000 uf at 10 V) whose other end is connected to the center tap of T1. This point is defined as circuit ground. C3 is charged by U3 to a peak voltage of about 8 V. This voltage is also applied to the input terminal of voltage regulator, U4 (typically a National Semiconductor LM78L05). The "GRD" terminal of U4 is also connected to T1 center-tap. The output pin of U4 is maintained at +5 VDC by the circuitry within U4. This point comprises the +5 V supply for the other circuits of the apparatus and is referred to hereinafter as the +5 V supply (FIG. 3). Capacitor C5 (typically a 0.1 uf at 15 V which is connected between U4 "out" and "GND") insures electrical stability of U4.

In like manner, except all electrical polarities are reversed, C4 (typically 470 uf at 10 V), U5 (typically National Semiconductor LM79L05) and C6 (typically a 0.1 uf at 15 V) comprise the −5 V supply for the other circuits of the apparatus and is referred to hereinafter as the −5 V supply (FIG. 3).

Figure 4:
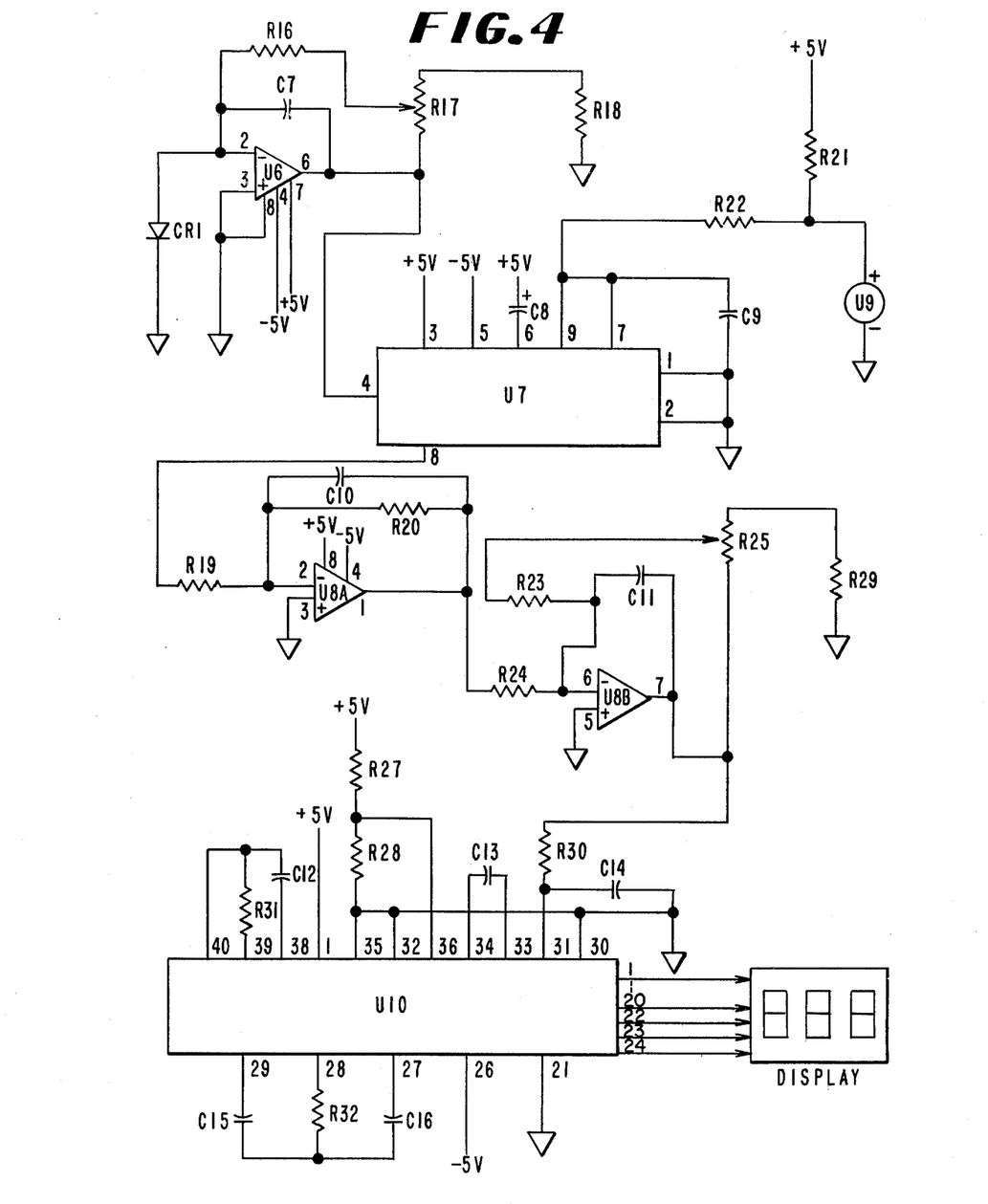

The output of the lamp L1 is impinged on the sample pouch under test and the light transmitted is sensed by photodetector CR1 (typically a UTC Model SD-5B). FIG. 4 is a schematic diagram of the other circuits used in the apparatus. CR1 is a silicon photodiode with cathode connected to ground and the anode is connected to amplifier, U6 inverting input pin 2. Pin 3, the non-inverting input of U6, is connected to ground. CR1 is operating into a virtual short circuit. When the CR1 photodiode is operated into a short circuit, it is capable of providing a current output linearly proportional to light input over 5 to 6 orders of magnitude of light brightness. The diode range in this configuration is from approximately $10^1$ uW/CM$^2$ (microwatts per centimeters squared) to approximately $10^{-5}$ uW/CM$^2$.

The amplifier U6 (typically an Analog Device AD515) is connected as a variable gain current-to-voltage converter. The output (Pin 6) is connected to one end of potentiometer, R17 (typically a 50K ohm potentiometer). The other end of R17 is connected to R18 (typically a 300 ohm, 1% metal film resistor) and the other end of R18 is connected to ground. The wiper of R17 is connected to R16 (typically a 499K ohm resistor). The other end of R16 is connected to the inverting input of U6. The +5 V supply and the −5 V supply (FIG. 3) are connected to the amplifier pins 7 and 4, respectively.

The output voltage of U6 is given by equation (4)

$$V_o = I_c Z_f \quad (4)$$

where:
 $V_o$=output voltage, volts
 $I_c$=photocell current into amplifier, amperes
 $Z_f$=effective impedance between pin 6 and pin 2 of U6, ohms The effective impedance, $Z_f$, depends on the setting of the potentiometer, R17, and varies from 499K ohms to 83 megohms. In operation, R17 is adjusted during zeroing to provide approximately 3 V output. Capacitor C7 (typically a 0.1 uf at 50 V) is used to reduce amplifier bandwidth and hence, noise. Amplifier U6 is chosen primarily for its low input bias current of about 1 picoamp because the bias current is a direct error source for the measurement.

The output of U6 is connected to the input, pin 4 of the logging circuitor logarithmic response circuit, U7 (typically an Analog Devices Model AD 536). Its transfer function is given in above equation (2). The reference terminal, pin 9, of U7 is connected to a precision voltage regulator, U9 (typically a National Semiconductor LM336Z), through a scaling resistor R22 (typically 180K ohm). The output of U9 represents the transmitted or reference level of illumination in the Beer-Lambert Law equation. When the front panel "Zero" potentiometer is adjusted during zeroing to provide an output equal to the output of U9, the output of U7 becomes zero because the logarithm of (1) is zero. U9 is powered from the +5 V supply (FIG. 3) through R21 (typically a 1K ohm, 5%) one end of which is connected to +5 V supply and the other end to the positive end of U9. The negative end of U9 is connected to ground. The voltage at the positive end of U9 is a constant 2.5 volts and is also connected to one end of a reference resistor, R22. The other end of R22 is connected to the reference terminal pin 9, of U7 and injects a reference current into U7. Pin 9 is also connected to pin 7 and to one end of a capacitor, C9 (typically a 0.001 uf at 15 V). The other end of C9 is connected to ground as are pins 1 and 2 of U7. These are the grounds of the device. The function of C9 is to provide stability to U7 internal circuitry. C8 (typically a 10 uf at 10 V) is connected between pin 6, U7 and +5 V supply (FIG. 3) and is a filter capacitor which removes any noise from output signals from U7. Pin 3 of U7 is connected to the +5 V supply (FIG. 3) and pin 5 of U7 is connected to the −5 V supply (FIG. 3). The output of U7 is provided at pin 8.

During measurements, the output of U6 becomes smaller than the reference value and the output of U7 becomes a negative value proportional to logarithm of the ratio of the input divided by the reference value.

The output of U7 is connected to the input of amplifier U8A. Amplifier U8A, resistors, R19 and R20, form a scaling and temperature compensating stage. The output (at pin 8) of the logging circuit, U7, has a scale factor of −3 MV/dB and has a negative temperature coefficient of 0.3%/°C. U8A increases the scale factor by a factor of 36, dictated by the ratio R20 to R19. R19 is a special resistor with a negative temperature coefficient of −0.3%/°C. which, because of its placement in U8A's feedback loop, just cancels U7's negative temperature coefficient. Capacitor C10 reduces U8A bandwidth and hence, noise.

The output of U7 is connected to a special temperature compensating resistor, R19 (typically a TELabs Model QB-1, 1K ohm). R19 is connected to the inverting input (pin 2) of amplifier U8A (typically ½ a Texas Instruments TIL082CP) connected in an inverting configuration. A feedback resistor, R20 (typically a 36K ohm, 1% metal film resistor), is connected between the output Pin 1 of U8A and its inverting input, Pin 2. The non-inverting input, Pin 3, is connected to ground. +5 V supply (FIG. 3) and −5 V supply (FIG. 3) are connected to pins 8 and 4, respectively, power the amplifier U8A. Capacitor, C10 (typically a 0.1 uf at 15 V disc capacitor) connected between the inverting input (pin 2) and output (pin 1) of U8A decreases frequency bandwidth of the stage. The overall combination provides an amplifier stage with an inverting gain of approximately −36.

The output of U8A, at pin 1, feeds amplifier U8B which is connected in a variable gain configuration. The gain of this stage is determined by equation (5).

$$A_v = (Z_f/Z_i) \quad (5)$$

where:
$A_v$ = voltage gain of the amplifier, volts/volt
$Z_f$ = effective value of resistance between pins 6 and 7 of U8B, ohms
$Z_i$ = input resistance, ohms The effective value of $Z_f$ is determined by the setting of the spanning adjustment (FIG. 1) potentiometer, R25, R23 and R29. The range of effective values extend from 10K ohms to 8 megohms. This provides a gain range for the stage of about 0.05 to 40 or 800 to 1.

The output voltage signal from U8A, pin 1, is connected to R24 (typically a 200K ohm, 1% metal film resistor). The opposite end of R24 is connected to the inverting input, pin 6, of the amplifier U8B (typically ½ TIL082CP). The non-inverting input of U8B, pin 5, is connected to ground. A potentiometer, (labelled Spanning Adjustment FIG. 1), R25 (typically a 100K, 10 turn potentiometer) has one end connected to the output, pin 7, of U8B. The opposite end is connected to one end of R29 (typically a 125 ohm, 1% metal film resistor) whose opposite end is connected to ground. The wiper of R25 is connected to one end of R23 (typically a 10K ohm, 1% metal film resistor) whose opposite end is connected to the inverting input, pin 6 of U8B. Capacitor C11, (a 0.1 uf at 15 V ceramic disc capacitor) is connected between the output pin 7 of U8B and its inverting input, pin 6.

Movement of the wiper of R25 closer to pin 7 of U8B decreases the effective impedance between pin 7 and pin 6 and thus, the gain of the stage. Conversely, moving the wiper toward the R29 end of the pot increases the effective impedance, and hence, increases the gain.

Proper adjustment of gain of U8B permits scaling of measurements directly in engineering units such as "PPM-HRS" (parts per million per hour).

The scaled output U8B, pin 7, is connected to the input of digital voltmeter which is an integrated circuit U10 (typically an Intersil 7107 integrated circuit). The function of U10 is to convert analog voltages, proportional to chemical dosages, into digital form. The conversion is accomplished inside U10. U10 is a 3½ digit analog to digital converter integrated circuit with integral display driver. Pin 36 is its reference voltage pin and the voltage at this point determines the devices full scale input range. Resistors R27 and R28 (typically a 3.1K ohm and 2K ohm, 1% metal film resistors) make up a voltage divider which produces a voltage of 1.25 volts at pin 36. One end of R27 is connected to +5 V supply (FIG. 3) and the opposite end is connected to one end of R28 and simultaneously, to pin 36. The opposite end of R28 is connected to ground as are pins 35, 32, and 30 of U10. Resistor R31 (typically a 100K ohm, 5%, carbon resistor) is connected on one end to pin 39 while the opposite is simultaneously connected to pin 40 of U10 and one end of capacitor C12 (typically a 100 pf (picofarad) at 15 V ceramic disc capacitor). The other end of C12 is connected to pin 38 of U10. The resistor capacitor network formed by R31 and C12 determine the internal clock frequency of U10 which in turn dictates its sampling rate. The clock frequency is typically 40 KHZ.

One end of resistor R32 (typically 1 megohm, 1% metal film resistors) is connected to pin 28 of U10. The opposite end is connected to one end of an integrating capacitor, C16 (typically a 0.01 uf at 63 V polystyrene capacitor) and simultaneously to a capacitor, C15 (typically a 0.1 uf at 15 V disc). The opposite end of C16 is connected to pin 27, U10, while the opposite end of C15 is connected to pin 29, U10. R32 and C16 determine the time constant of an integrating network in U10 (typically 10 milliseconds) while C15 insures stability of certain internal circuitry.

Capacitor C13 (typically a 0.1 uf at 15 V disc capacitor) provides noise decoupling inside U10 and is connected across pins 33 and 34 of U10. Power is supplied to U10 at pins 26 and 1 for −5 V and +5 V supply, respectively.

Resistor R30 (typically a 1 MEG, 5%, carbon resistor) is connected at one end to the output of U8B, pin 7, while the opposite end is connected to pin 31 of U10 which is U10 analog input terminal. Pin 31 is also connected to one end of capacitor C14 (typically a 0.1 uf at 15 V ceramic disc capacitor). The opposite end of C14 is connected to ground. The combination of R30 and C14 comprise a low pass filter which reduces signal noise. Its cutoff frequency is typically 10 HZ.

U10 has, as outputs, twenty four control lines (Terminals 1 through 24) which, when used in concert with three light emitting diode numerical displays (typically Monsanto type MAN4610), can display all number combinations between "000" and "999" plus three decimal points. These display devices are well known in the art.

In the operation of the apparatus the selector switch (S1, FIG. 3) is positioned to provide the correct brightness level to the lamp and the proper color interference filter. It is preferred to have the color interference filter mechanically geared to the selector switch so that the brightness level of the lamp is matched with the correct color interference filter. Predetermined brightness levels that give the most accurate readings along with the proper color interference filter are given for sample pouches containing different chemicals for the various types of gases measured.

A calibration card having two openings is provided in which one opening is covered with a transparent film that has an opaqueness that corresponds to a value for the spanning adjustment and the other opening is covered with a transparent film for the zero adjustment. A calibration card is provided for each set of sample pouches to be measured.

To adjust the apparatus, the calibration card is inserted into the instrument and an adjustment to the spanning adjustment is made to provide a readout shown on the card and then the card is turned and the zero adjustment is made. This procedure is done for about 3–9 times until the spanning adjustment readout and the zero readout become constant.

The values of the sample pouches then are measured. First, the reagent section of the pouch is broken and mixed with the other constituent in the pouch and then the pouch is inserted into sample pouch holder and the light transmission of the pouch is measured which is directly converted into engineering units by the apparatus such as parts per million per hour. These readings are recorded for each pouch and a record for each worker is kept that shows a dosage, if any, worker was exposed to during a work period.

Some of the advantages of the apparatus over prior art instruments are that the apparatus is relatively accurate, is portable, is of a durable construction, can easily be adjusted and zeroed and can be operated by personnel with low levels of training. Compared to prior art instruments, there is no delicate reference circuit that must be maintained to provide accurate readings but a relatively simple adjustment and zeroing procedure is used which is directly related to the pouches to be measured that provides a good level of accuracy for readings that are obtained.

We claim:

1. An apparatus which measures light transmitted through a fluid sample by a photodetector and electronically converts a signal from the photodetector to a signal that is displayed on a readout device, wherein the apparatus contains a power source, a light source connected to a power source, a photodetector, a sample holder for a fluid sample that forms a cell of a constant thickness through which light from the light source passes and is measured by the photodetector and a readout device; the improvement used therewith in the absence of a reference light beam comprises:

(a) a color interference filter positioned between the sample holder and the photodetector which filters all colors from the light transmitted through the sample except a band of colored light that is to be measured;

(b) a converter electrically connected to the photodetector which converts a current signal from the photodetector to a voltage signal;

(c) a logarithmic response circuit electrically connected to the converter that changes the voltage signal from the converter into a logarithmic signal proportional to the logarithm of the voltage signal;

(d) a digital voltmeter electrically connected to the logarithmic response circuit that converts the signal from the logarithmic response circuit to a signal displayed on the readout device;

(e) a selector switch having multiple positions each connected to a resister of a different value is positioned between the power source and the light source to provide a light source of varying intensity and the selector switch is mechanically coupled to a disc of multiple color interference filters such that the light source matches the color interference filter required for a particular light source;

(f) a gain adjustment is electrically connected to the converter which is a zeroing device that upon adjustment brings the readout device to a zero reading;

(g) a temperature compensator circuit is electrically connected to the logging circuit and the digital voltmeter in which the temperature compensator circuit adjusts the electrical signal received from the logging circuit to eliminate any variations in the signal caused by temperature variations; and (h) a spanning adjustment circuit electrically connected to the temperature compensator circuit and the digital voltmeter to convert the electrical signal from the temperature compensator circuit into engineering units that can be displayed directly on the readout device.

2. The apparatus of claim 1 in which a pouch holder is used which is a center hinged case having pressure pads therein and opening in the case to permit a light beam from the light source to pass through; wherein a pouch containing a fluid sample which is to be measured by said apparatus is placed in the pouch holder and the pouch holder is folded together on a cell or constant thickness is formed through which the light beam passes.

3. The apparatus of claim 1 in which the photodetector is a silicon photodiode.

4. A process for operating an apparatus which measures light transmitted through a fluid sample by a photodetector and electronically converts a signal from the photodetector to a signal that is displayed on a readout device, wherein the apparatus contains a power source, a light source connected to a power source, a photodetector, a sample holder for a fluid sample that forms a cell of a constant thickness through which light from the light source passes and is measured by the photodetector and a readout device; the improvement used therewith in the absence of a reference light beam comprises (a) a color interference filter positioned between the sample holder and the photodetector which filters all colors from the light transmitted through the sample except a band of colored light that is to be measured;

(b) converter electrically connected to the photodetector which converts a current signal from the photodetector to a voltage signal;
(c) a logarithmic response circuit electrically connected to the converter that changes the voltage signal from the converter into a logarithmic signal proportional to the logarithm of the voltage signal
(d) a digital voltmeter electrically connected to the logarithmic response circuit that converts the signal from the logarithmic response circuit to a signal displayed on the readout device;
(e) a selector switch having multiple positions each connected to a resister of a different value is positioned between the power source and the light source to provide a light source of varying intensity and the selector switch is mechanically coupled to a disc of multiple color interference filters such that the light source matches the color intereference filter required for a particular light source;
(f) a gain adjustment is electrically connected to the converter which is a zeroing device that upon adjustment brings the readout device to a zero reading;
(g) a temperature compensator circuit is electrically connected to the logging circuit and the digital voltmeter in which the temperature compensator circuit adjusts the electrical signal received from the logging circuit to eliminate any variations in the signal caused by temperature variations; and
(h) a spanning adjustment circuit electrically connected to the temperature compensator circuit and the digital voltmeter to convert the electrical signal from the temperature compensator circuit into engineering units that can be displayed directly on the readout device which process comprises:
  (1) calibrating the apparatus with a calibration card by repeatedly adjusting the spanning adjustment to read out a value of the calibration card and zeroing the readout until the readings are stabilized.
  (2) adjusting the selector switch to the desired light intensity with the proper color interference fitter;
  (3) inserting a sample pouch into the sample holder after ingredients in the pouch have been throughly mixed; and
  (4) recording the readout value of the pouch from the readout device.

* * * * *